(12) United States Patent
Haidukewych (10) Patent No.: US 9,615,865 B2
(45) Date of Patent: Apr. 11, 2017

(54) BONE END (EPIPHYSIS) FRACTURE FIXATION DEVICE AND METHOD OF USE

(71) Applicant: George J. Haidukewych, Orlando, FL (US)

(72) Inventor: George J. Haidukewych, Orlando, FL (US)

(*) Notice: Subject to any disclaimer, the term of this patent is extended or adjusted under 35 U.S.C. 154(b) by 521 days.

(21) Appl. No.: 13/986,058

(22) Filed: Mar. 28, 2013

(65) Prior Publication Data

US 2014/0296855 A1 Oct. 2, 2014
US 2017/0049490 A9 Feb. 23, 2017

Related U.S. Application Data

(60) Division of application No. 12/583,908, filed on Aug. 27, 2009, now abandoned, which is a continuation of application No. 11/897,647, filed on Aug. 31, 2007, now abandoned.

(60) Provisional application No. 60/927,667, filed on May 4, 2007.

(51) Int. Cl.
```
A61B 17/74   (2006.01)
A61B 17/17   (2006.01)
A61B 17/86   (2006.01)
A61B 17/80   (2006.01)
```

(52) U.S. Cl.
CPC ........ *A61B 17/746* (2013.01); *A61B 17/1721* (2013.01); *A61B 17/8685* (2013.01); *A61B 17/8057* (2013.01)

(58) Field of Classification Search
CPC .. A61B 17/748; A61B 17/746; A61B 17/1721
USPC ......................................................... 606/281
See application file for complete search history.

(56) References Cited

U.S. PATENT DOCUMENTS

| | | | | |
|---|---|---|---|---|
| 2,414,882 | A * | 1/1947 | Longfellow | 606/65 |
| 5,395,371 | A * | 3/1995 | Miller et al. | 606/287 |
| 5,667,510 | A * | 9/1997 | Combs | 606/86 R |
| 6,692,496 | B1 * | 2/2004 | Wardlaw | 606/64 |
| 7,837,717 | B2 * | 11/2010 | Deffenbaugh et al. | 606/281 |
| 2007/0191855 | A1 * | 8/2007 | Orbay et al. | 606/87 |
| 2007/0299448 | A1 * | 12/2007 | Chin et al. | 606/69 |
| 2008/0275508 | A1 * | 11/2008 | Haidukewych | A61B 17/746 606/280 |
| 2010/0036431 | A1 * | 2/2010 | Haidukewych | A61B 17/746 606/286 |

* cited by examiner

*Primary Examiner* — David Bates
(74) *Attorney, Agent, or Firm* — Arthur W. Fisher, III (57) ABSTRACT

A bone end (epiphysis) fracture device including a rotatable fixation plate having a guide pin aperture and a plurality of fixation screw apertures formed therethrough. The guide pin aperture is used by a surgeon to position the fixation plate so that one or more fixation screw apertures are properly positioned to receive fixation screws inserted by the surgeon for repairing a bone end fracture. In another embodiment, the fracture fixation device also includes a side plate to which the fixation plate is rotatably attached. This embodiment further includes one or more side plate apertures formed through an elongate extension, whereby the fixation device may also be attached to the bone for which an end fracture is being repaired. A lock screw is provided in this embodiment for locking the position of the fixation plate with respect to the side plate.

1 Claim, 10 Drawing Sheets

BONE END (EPIPHYSIS) FRACTURE FIXATION DEVICE AND METHOD OF USE

CROSS-REFERENCE

This is a divisional application of pending application Ser. No. 12/583,908 filed Aug. 27, 2009 which is a continuation application of pending application Ser. No. 11/897,647 filed Aug. 31, 2007 that claims the benefit of prior Provisional Application Ser. No. 60/927,667 filed May 4, 2007.

BACKGROUND OF THE INVENTION

Field of the Invention

The present invention relates to an improved fixation device for fractures of the ends of bones (epiphysis), and is described in a preferred embodiment with respect to a femoral neck fracture, and its method of use is also disclosed.

Description of the Prior Art

The use of various plates and bone screws for fixing bone fractures is old and well known in the art. In fact, prior art patents teach numerous devices for fixing a fracture of bone ends such as the femoral neck.

For example, U.S. Patent Application Publication No. 2004/0102778 to Huebner shows bone plates having an adjustable joint, and methods of using the bone plates to fix bones. The bone plates each may include a plurality of plate members connected by an adjustable (pivotable and/or translational) joint. The adjustable joint may be configured so that the shape and/or extent of the bone plate may be changed by adjusting the angular disposition of the plate members. The angular disposition may be adjusted by pivotal movement of a plate member about one axis or about a plurality of axes, and then the angular disposition may be fixed (locked). Each plate member may define one or more openings. The plate members may be configured to be secured to different regions of one bone or secured to different bones using fasteners placed in the openings.

U.S. Patent Application Publication No. US 2006/0217711 to Stevens, et al., discloses a locking plate that extends along the length of the femur and provides apertures for inserting a plurality of bone anchor screws into the femoral head and across the fracture. Similar structure is also disclosed in U.S. Patent Application Publication No. US 2005/0101959 to Mitkovic. U.S. Pat. No. 5,871,485 to Rao, et al., discloses and teaches yet another device for fixing a fracture of the femoral head. Yet another device, also employing a fixation screw that extends into the femoral head across the fracture is disclosed in U.S. Pat. No. 6,139,552 to Horiuchi.

Additional examples are found in U.S. Pat. No. 5,681,313 to Diez, et al.; U.S. Pat. No. 7,090,676 B2; U.S. Pat. No. 7,326,212 B2; U.S. Patent Application Publications 2006/0217711 A1 and 2008/0140128 A1.

It is therefore quite clear that prior art patent literature teaches a variety of devices and attendant methods for surgically fixing fractures of the femoral neck. Just as apparent is the fact that these prior art devices possess virtually no means for adjusting a particular device to the needs of a particular patient. Variables such as size of the femur and the femoral head and the position and orientation of the femoral head fracture must be considered in the doctor's decision-making process with regard to placement and use of a fixation device. In addition to these variables, the doctor must also consider the health condition of the bone itself.

It is therefore clear that there remains a need in the art of femoral neck fracture fixation devices and methods of use for a device that is capable of adjustment to suit the needs of a particular patient. Such an adjustable device would not only prove to be more economical, but would also provide better care when fixation of a femoral neck fracture was needed.

It is also to be understood that this invention is not limited to fixation of femoral neck fractures, but is adaptable to use for fixing a variety of bone end (epiphysis) fractures. The drawing figures and detailed description relate to a femoral neck fracture for the purpose of clearly describing preferred embodiments of the invention.

SUMMARY OF THE INVENTION

The present invention relates to a bone end (epiphysis) fracture fixation device and its method of use. The fixation device of this invention is particularly characterized by its construction to permit radial adjustability of a fixation plate through which a plurality of fixation screws may be inserted for the purpose of fixing the bone end fracture. Means are also provided for aligning the device according to the patient's needs. In a second embodiment, the rotatable fixation plate is movably mounted on a side plate, whereby the device may also be attached to the patient's bone away from the end fracture, should that be deemed necessary by the doctor. A method for using the bone end (epiphysis) fracture fixation device of the present invention, in both a primary and secondary embodiment, is also disclosed with regard to a femoral neck fracture.

The invention accordingly comprises the features of construction, combination of elements, and arrangement of parts which will be exemplified in the constructions hereinafter set forth, as well as the several steps and the relation of one or more of such steps with respect to each of the others thereof, which will be exemplified in the methods hereinafter disclosed, for using the invention.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION

Figure 1:
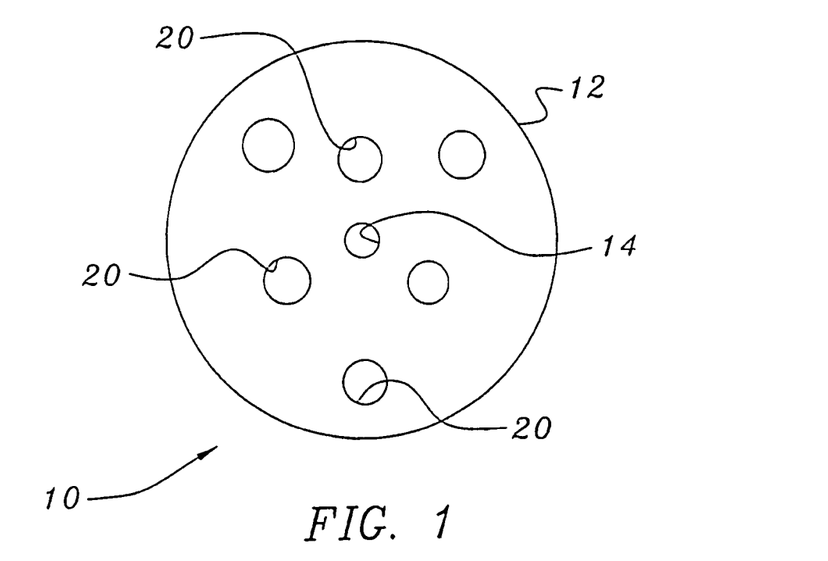
FIG. 1 is a plan view of a first preferred embodiment for the bone end (epiphysis) fracture fixation device of this invention.

Referring to the view of FIG. 1, a first preferred embodiment of the bone end (epiphysis) fracture fixation device is generally indicated as 10. Device 10 comprises a substantially planar and substantially circular fixation plate 12. Use of the phrase "substantially circular" is meant to describe that the perimeter of fixation plate 12 is not to be limited to that geometry. Virtually any geometric shape could be used. In similar fashion, use of the phrase "substantially planar" is intended to indicate that fixation plate 12 might define a curved plane, depending upon the topography of the patient's bone to which the plate 12 is being applied.

Figure 3:
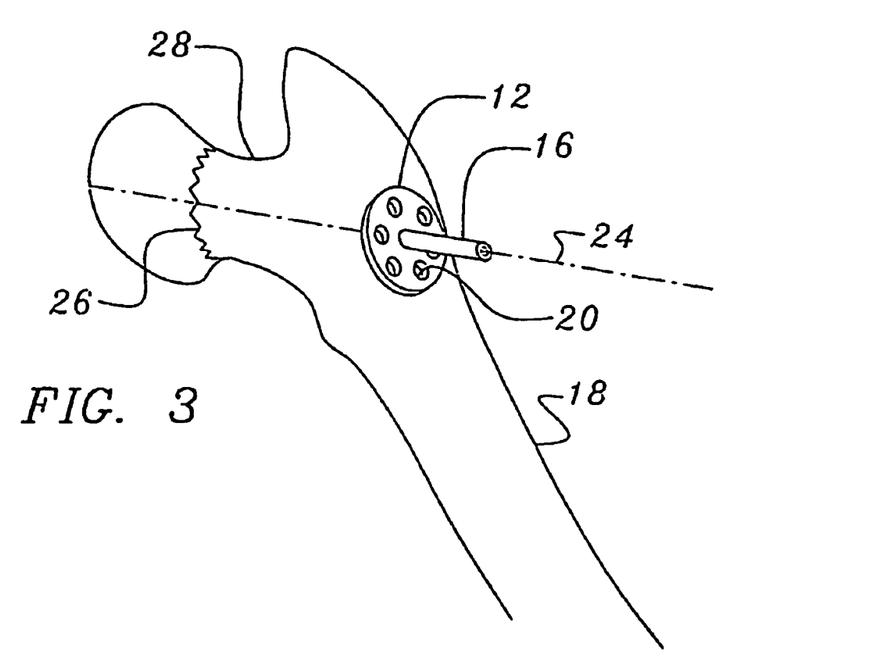
FIG. 3 is a fragmentary view of a patient's femur having a neck fracture, illustrating the use of a guide pin to position the fixation plate.

Still referring to the first preferred embodiment of FIG. 1, a guide pin aperture 14 extends through plate 12 and is used by the surgeon in combination with a guide pin 16 (FIG. 3) to position fixation plate 12 properly on the patient's femur 18 (FIG. 3).

As also clearly seen in the view of FIG. 1, fixation plate 12 further comprises a plurality of fixation screw apertures 20, and each of these screw apertures 20 extend through fixation plate 12 whereby a fixation screw, generally indicated as 22 in the view of FIG. 2, may be inserted, as is more fully described below. While a plurality of fixation screw apertures 20 are provided through fixation plate 12, the exact size and relative placement of the illustrated screw apertures 20 are not to be interpreted as limiting factors to the scope of the present invention. The size of each of the screw apertures 20 is such that a fixation screw 22 may be operatively inserted therethrough. The relative placement of screw apertures 20 may define patterns other than the substantially triangular pattern of six screw apertures 20 as shown in FIG. 1.

Figure 4:
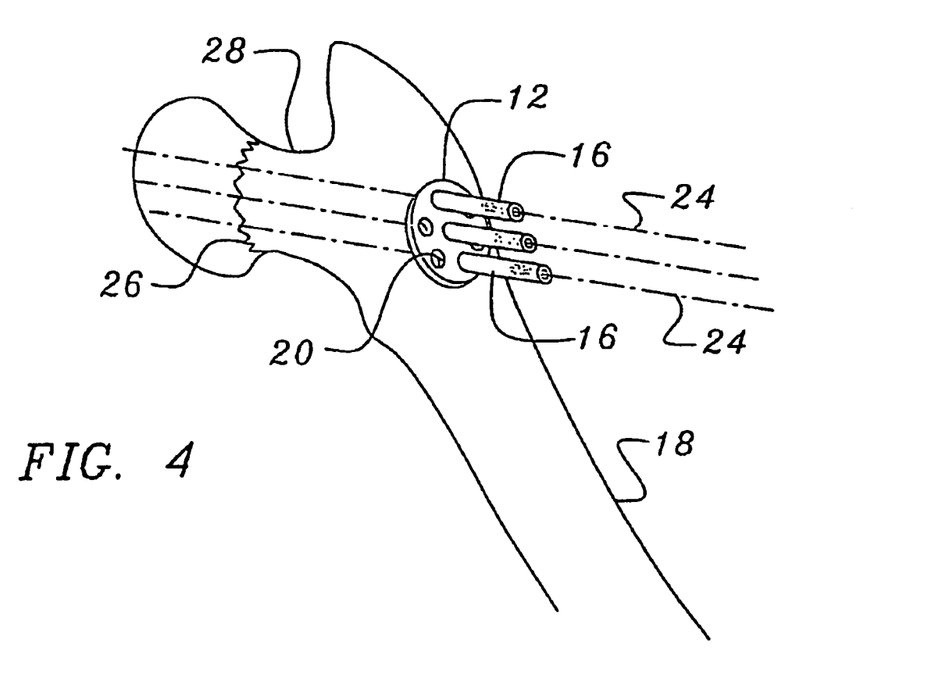
FIG. 4 is a view similar to that of FIG. 3 illustrating the use of three guide pins for orientating the fixation plate of the present invention.

Referring to the view of FIG. 3, one can see that a guide pin 16 has been attached to guide pin aperture 14, and a guide wire 24 has been inserted by the surgeon for initial placement of fixation plate 12 on femur 18. This procedure takes place following standard pre-op diagnosis to determine the location and nature of fracture 26 of the femoral neck 28 to provide proper initial placement of fixation plate 12. Once positioned as shown in FIG. 3, fixation plate 12 may be rotated about the axis defined by guide pin 16 and guide wire 24 in order to position one or more of the fixation screw apertures 20 for desired operative attachment of one or more fixation screws 22 (not shown in FIG. 3). Thus, one of the unique features of this invention is the ability of the surgeon to use a single fixation plate 12 to locate quite precisely the optimum positioning of one or more fixation screws 22. As shown in the view of FIG. 4, it is clearly within the scope of the present invention to employ a plurality of guide pins 16 and guide wires 24 in combination with not only the guide pin aperture 14 but also fixation screws apertures 20 to "lock" fixation plate 12 in position on the patient's femur 18 prior to insertion of fixation screws 22 as deemed appropriate by the surgeon.

Figure 5:
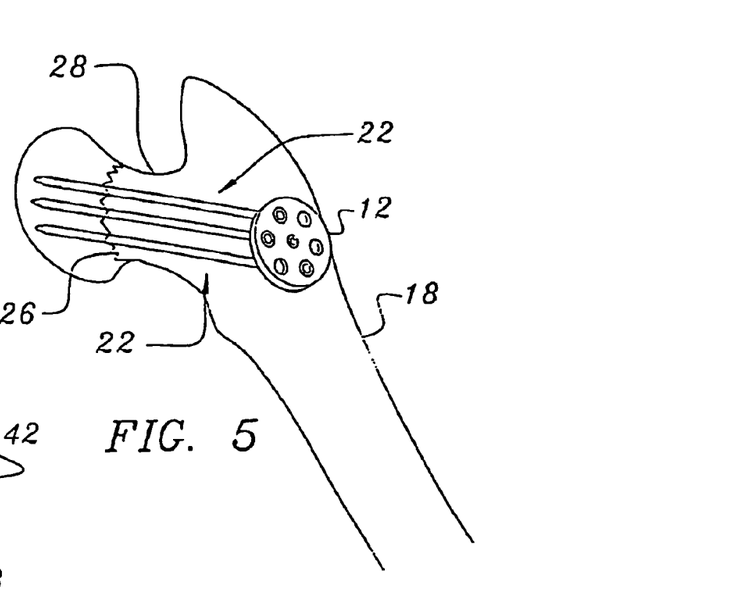
FIG. 5 is a view similar to that of FIG. 3 illustrating the use of three fixation screws in combination with the fixation plate to fix a femoral neck fracture.

As shown in the view of FIG. 5, after inserting the fixation screws 22, guide pins 16 and guide wires 24 are removed by the surgeon, and fracture 26 is "fixed."

Figure 2:
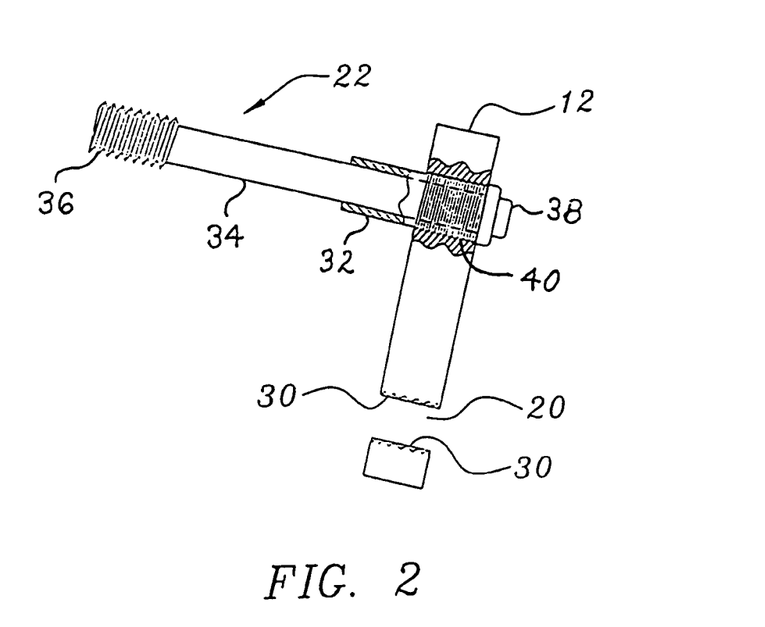
FIG. 2 is a side elevation illustrating the placement of one fixation screw through the fixation plate.

Considering the view of FIG. 2, one can see that the interior wall defined by each of the fixation screw apertures 20 is preferably threaded, as indicated at 30. Fixation screw 22 comprises a screw body 34 having a barrel 32 mounted thereon such that screw body 34 may rotate therein and such that the longitudinal axis of screw body 34 corresponds to the longitudinal axis of barrel 32. Distal end 36 of fixation screw 22 is threaded and proximal end 38 is appropriately configured to receive a tool (not shown) for the purpose of inserting and tightening screw body 34 to fix fracture 26 as best seen in the view of FIG. 5. Proximal end 40 of barrel 32 is threaded to be received and engaged by the threads 30 of fixation screw aperture 20. Thus, when barrel 32 is attached to a corresponding fixation screw aperture 20, and a corresponding screw body 22 is inserted through barrel 32, the alignment of screw body 34 is maintained as previously determined by the surgeon for proper placement across fracture 26 to secure and fix the femoral neck 28. While the view of FIG. 5 illustrates the use of three fixation screws 22, it is to be understood that one or more fixation screws 22 may be used within the scope of the present invention, depending upon the surgeon's evaluation of necessary steps to fix fracture 26.

It is, however, to be understood that the treads 30 of fixation screw apertures 20 are preferable, but not required. Of course, if the device were constructed to eliminate threads 30, there would be no need for threading proximal end 40 of barrel 32.

Figure 6:
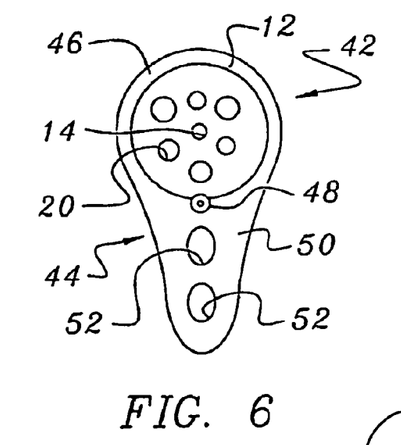
FIG. 6 is a plan view of a second preferred embodiment for the device of this invention, including a fixation plate rotatably attached to a side plate.
Figure 7:
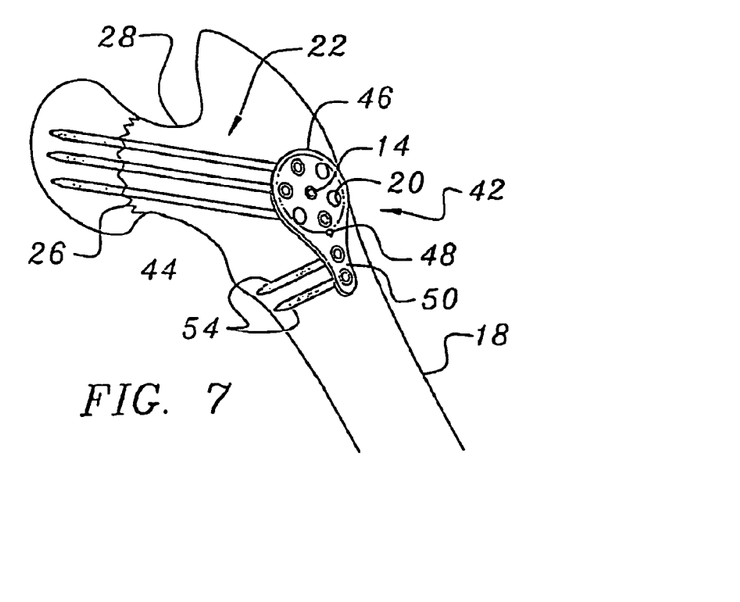
FIG. 7 is a view similar to that of FIG. 5 showing use of the second preferred embodiment of this invention with three fixation screws operatively mounted across a femoral neck fracture and two side plate screws inserted into the patient's femur.

Attention is now invited to the views of FIGS. 6 and 7. These figures show a second preferred embodiment for the femoral neck fracture fixation device of this invention, generally indicated as 42. However, structural elements that are substantially identical to those described previously with regard to first preferred embodiment 10 are indicated by like reference numerals.

As clearly seen in the views of FIGS. 6 and 7, second preferred embodiment 42 comprises not only a fixation plate 12, but also a side plate generally indicated as 44. Fixation plate 12 of second preferred embodiment 42 is rotatably attached to enlarged end 46 of side plate 44. The rotational attachment of fixation plate 12 to enlarged end 46 is accomplished, preferably, by a rotatable attachment around guide pin aperture 14. It is also to be understood that enlarged end 46 of side plate 44 is relieved so that guide pin aperture 14 and the plurality of fixation screw apertures 20 extend through fixation plate 12 and through enlarged end 46. Because fixation plate 12 of the second preferred embodiment 42 is rotatably attached to side plate 44, second preferred embodiment 42 further comprises a lock screw 48 mounted on side plate 44 such that at least a portion of lock screw 48 will engage a portion of the perimeter of fixation plate 12 whereby tightening lock screw 48 will fix the relative position of the fixation screw apertures 20 with respect to the patient's femur. This permits the surgeon to position the fixation screw apertures properly, as determined in pre-op procedures, for insertion of the required number of fixation screws generally indicated as 22.

In both FIG. 6 and FIG. 7, one can also see that the elongated body 50 of side plate 44 comprises a plurality of side plate apertures 52 formed therethrough. With particular regard to the view of FIG. 7, it can be seen that side plate apertures 52 may be used to receive a corresponding side plate screw 54 therethrough and into the patient's femur, when necessary as determined by the surgeon, for the purpose of providing greater stability and strength to the second preferred embodiment 42 used for femoral neck fracture fixation.

Of course, it is to be understood that second preferred embodiment 42 is not to be limited to the particular geometric configuration shown in the views of FIGS. 6 & 7. In similar fashion, the scope of the present invention is not to be limited by the particular use of three fixation screws 62 or two side plate screws 54. Such specifics are determined by the surgeon after considering the patient's needs.

Finally, with regard to second preferred embodiment 42, it is also to be understood that an alternative rotatable attachment of fixation plate 12 to enlarged end 46 of side plate 44 may be accomplished wherein guide pin aperture 14, while extending through fixation plate 12, does not extend through enlarged end 46. In this construction, guide pin aperture 14 is used solely for the rotatable attachment of fixation plate 12 to enlarged end 46. Of course, with this type of construction, proper positioning of fixation plate 12 would be accomplished by the use of one or more guide pins 16 and corresponding guide wires 24 inserted through a corresponding one or more of the fixation screw apertures 20, substantially as shown in the view of FIG. 4.

Having thus set forth preferred embodiments for the femoral neck fracture fixation device of this invention, their method of use by the surgeon is substantially as follows. After normal pre-op investigation and determination by the surgeon, either first preferred embodiment 10 or second preferred embodiment 42 is selected and disposed on the patient's femur as illustrated in the several views of the drawings. Fixation plate 12 is positioned for the desired operative placement of fixation screws 22 and maintained in that position by the surgeon's use of one or more guide pins 16 and corresponding guide wires 24. With particular regard to second preferred embodiment 42, lock screw 48 would then be tightened.

Figure 16:
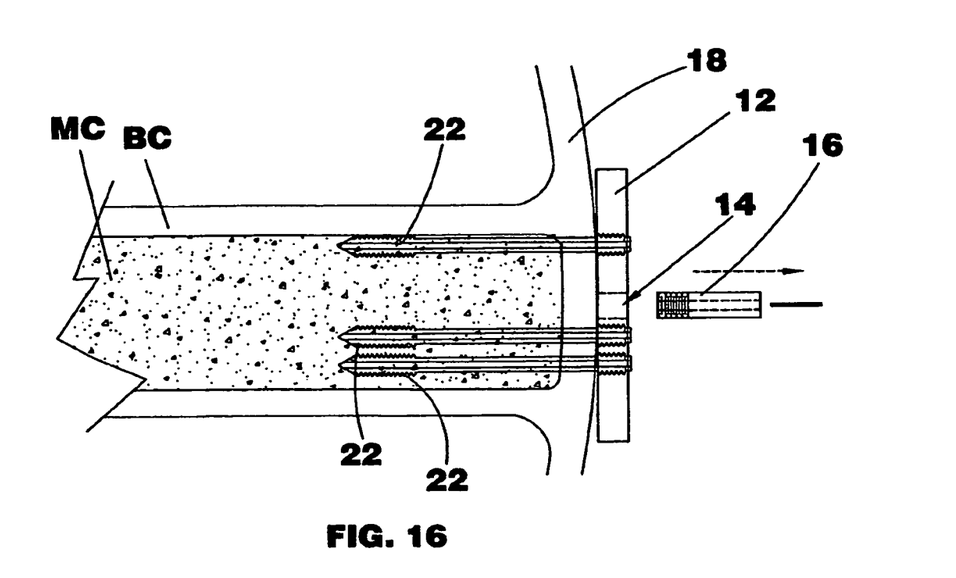
FIG. 16 is a partial cross-sectional side elevation view of the bone end (epiphysis) fracture fixation device of this invention as the alignment guide pin is removed from the fixation plate and the alignment guide pin is withdrawn from the marrow channel mc with the fixation screws anchored in the marrow channel mc.
Figure 17:
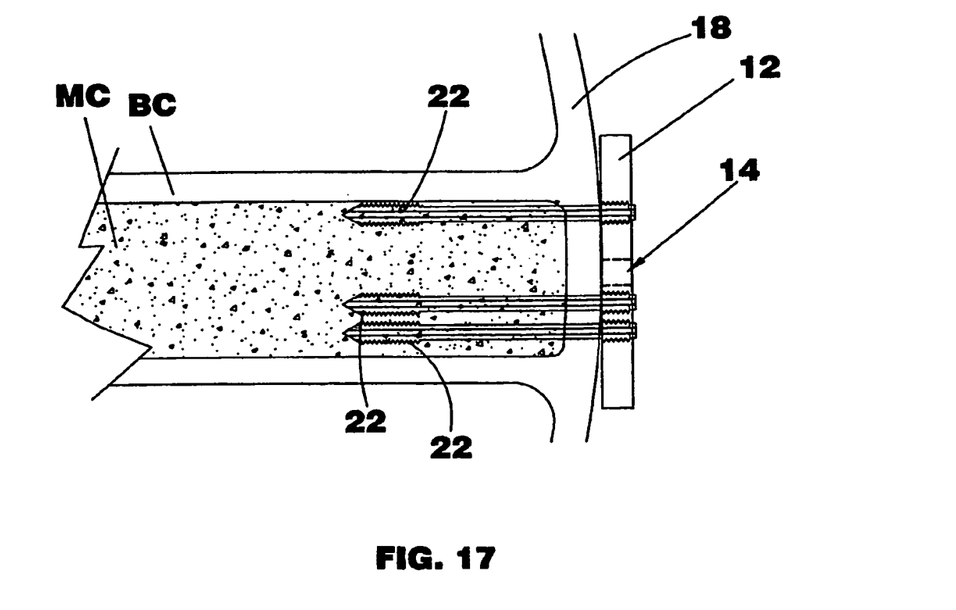
FIG. 17 is a partial cross-sectional side elevation view of the bone end (epiphysis) fracture fixation device of this invention with the fixation screws anchored in the fixation plate and the marrow channel mc.
Figure 18:
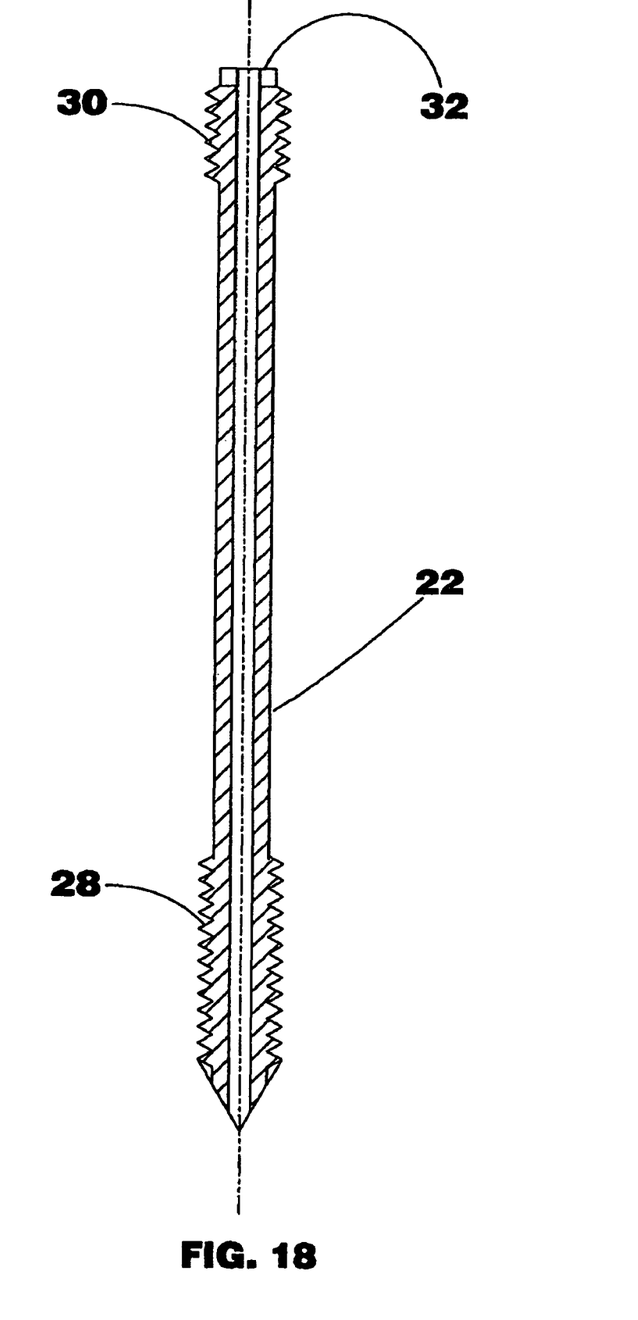
FIG. 18 is a cross-sectional side view of the fixation screw of this invention.

FIGS. 8 through 17 show the step by step method of placement and alignment of the substantially circular fixation plate 12 relative to the marrow channel mc within the bone cortex bc of the fractured femur 18 and to anchor the cannulated fixation screws 22 shown in FIG. 18 into the marrow channel mc.

Figure 8:
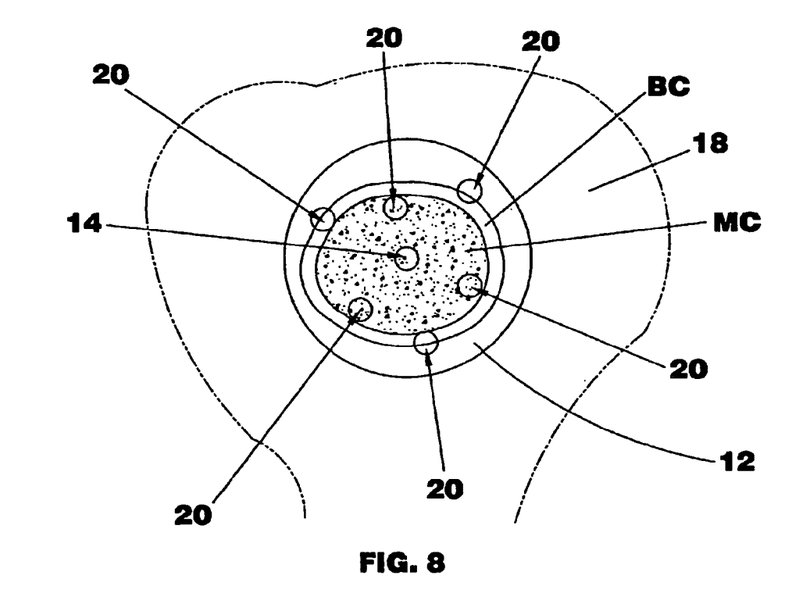
FIG. 8 is a plan view of the bone end (epiphysis) fracture fixation device of this invention operatively aligned or positioned on the patient's femur.

As previously described, the alignment guide pin aperture 14 extends through the fixation plate 12 and is used by the surgeon in combination with the alignment guide pin 16 to position or align the substantially circular fixation plate 12 properly on the patient's femur 18 relative to the marrow channel mc. Initially, the fixation plate 12 is centered in the marrow channel mc as shown in FIG. 8.

Figure 9:
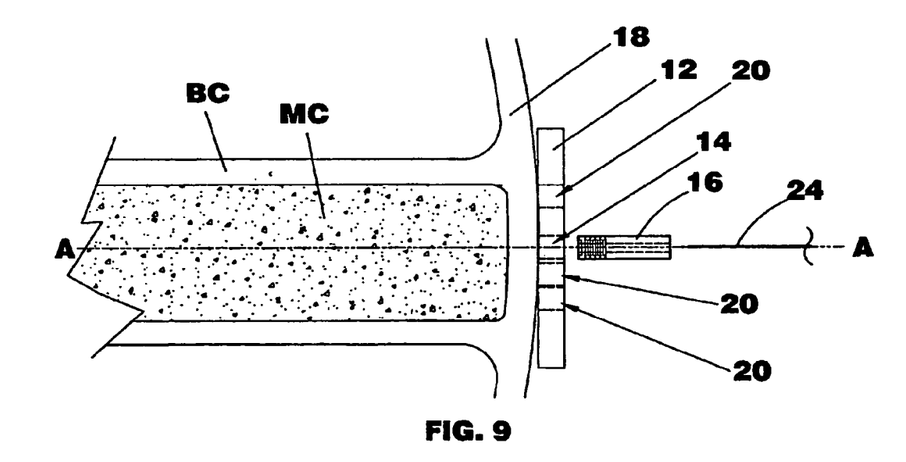
FIG. 9 is a partial cross-sectional side elevation view of the bone end (epiphysis) fracture fixation device of this invention as the alignment guide pin and the alignment guide wire are in operative position prior to being mounted to the fixation plate and inserted into the marrow channel mc respectively.
Figure 10:
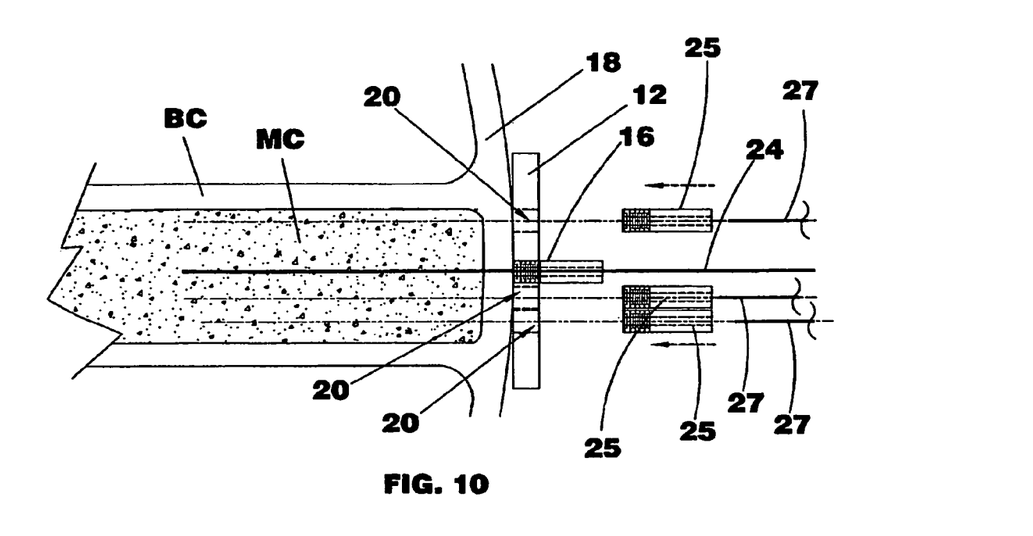
FIG. 10 is a partial cross-sectional side elevation view of the bone end (epiphysis) fracture fixation device of this invention with the alignment guide pin operatively mounted on the fixation plate and the alignment guide pin operatively inserted in the marrow channel mc with the fixation screw guide pins and fixation screw guide wires in operative position prior to being mounted to the fixation plate and inserted in the marrow channel mc respectively.

As shown in FIGS. 9 and 10, with alignment guide pin 16 coupled to the guide pin aperture 14, or mounted to fixation plate 12, the alignment guide wire 24 is inserted through the alignment guide pin 16 and into the marrow channel mc by the surgeon. This procedure takes place following standard pre-op diagnosis to determine the location and nature of fracture 26 of the femoral neck 28 to provide proper initial placement of the fixation plate 12 relative to the marrow channel mc and bone cortex bc. Then, the fixation plate 12 is rotated about the axis A-A of the alignment guide pin 16 and the alignment guide wire 24 to align or position one or more of the fixation screw apertures 20 to operatively receive a corresponding fixation screw as shown in FIG. 8.

Figure 11:
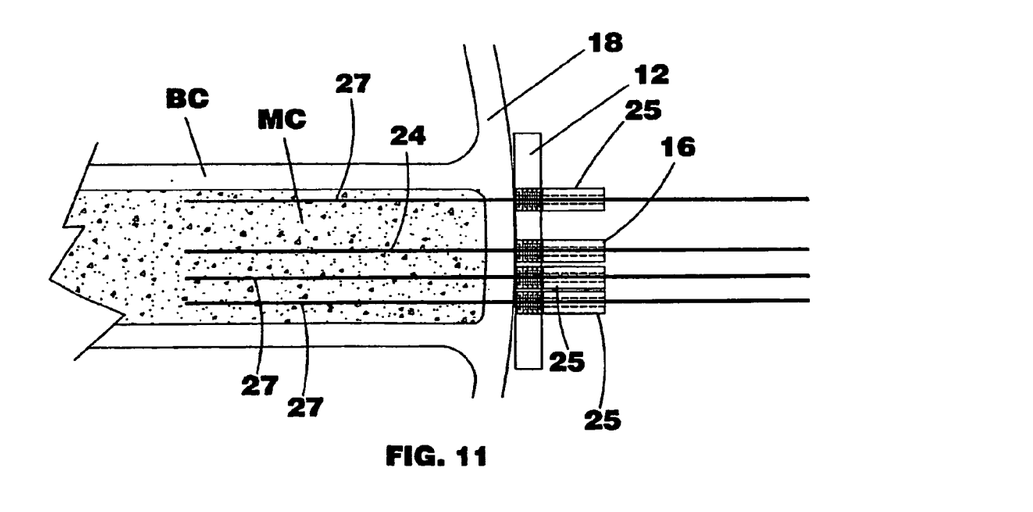
FIG. 11 is a partial cross-sectional side elevation view of the bone end (epiphysis) fracture fixation device of this invention with the alignment guide pin and fixation screw guide pins mounted to the fixation plate and the alignment guide pin and fixation screw guide pins operatively inserted in the marrow channel mc.

As shown in FIGS. 10 and 11, a plurality of fixation screw guide pins 25 are then coupled to the fixation screw apertures 20 or mounted on the fixation plate 12. A fixation screw guide wire 27 is then inserted through a corresponding fixation screw guide pin 25 and into the marrow channel mc to secure the fixation plate 12 in rotational position on the patient's femur 18 prior to insertion of the fixation screws 22 into the marrow channel mc.

Figure 12:
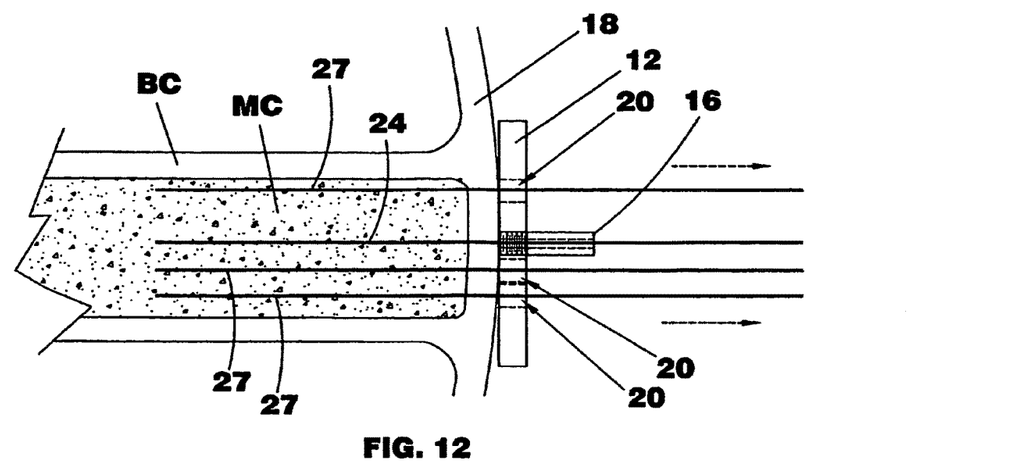
FIG. 12 is a partial cross-sectional side elevation view of the bone end (epiphysis) fracture fixation device of this invention with the alignment guide pin operatively mounted to the fixation plate and the alignment guide pin and fixation screw guide wires operatively inserted into the marrow channel mc with the fixation screw guide pins removed from the fixation plate.
Figure 13:
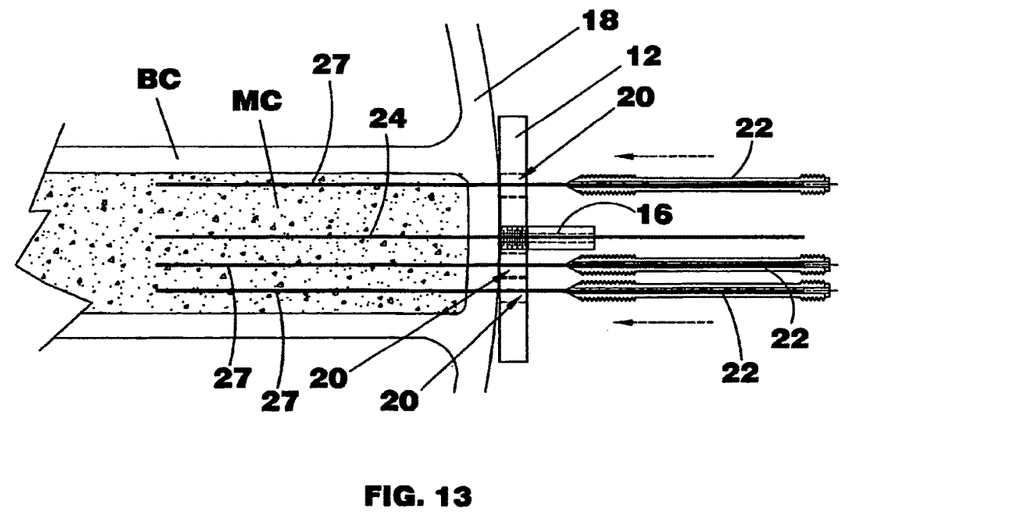
FIG. 13 is a partial cross-sectional side elevation view of the bone end (epiphysis) fracture fixation device of this invention with the alignment guide pin operatively mounted to the fixation plate and the alignment guide pin and fixation screw guide wires operatively inserted into the marrow channel mc with the fixation screws operatively aligned with the fixation screw apertures on the fixation screw guide wires prior to being inserted into the marrow channel mc.
Figure 14:
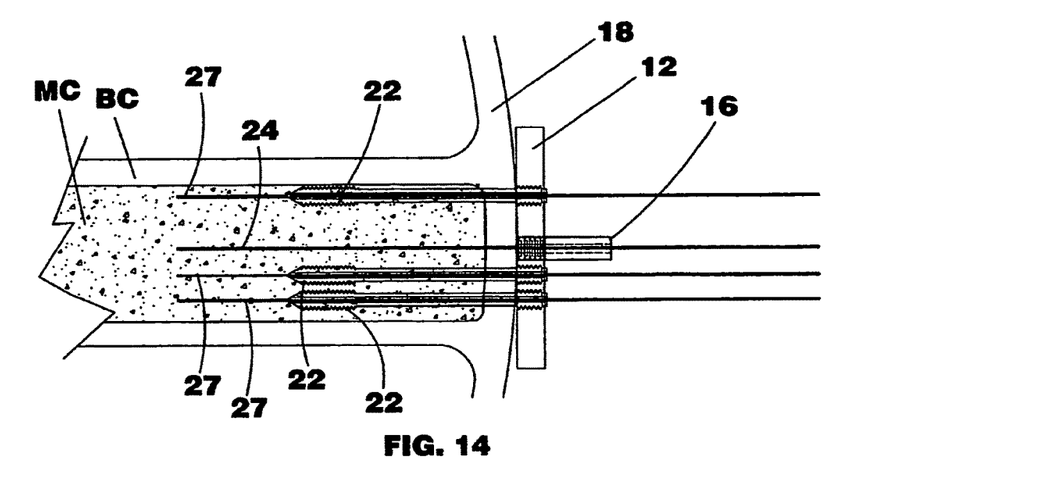
FIG. 14 is a partial cross-sectional side elevation view of the bone end (epiphysis) fracture fixation device of this invention with the alignment guide pin operatively mounted to the fixation plate with the alignment guide pin and fixation screw guide wires operatively inserted into the marrow channel mc with the fixation screws anchored in the marrow channel mc adjacent the bone cortex.

As shown in FIG. 12, the fixation screw guide pins 25 are removed from the fixation screw apertures 20 with each of the fixation screw guide wires 27 remaining embedded or inserted in the marrow channel mc. Then each cannulated fixation screw 22 is placed onto the corresponding fixation screw guide wire 27 and inserted into the marrow channel mc as shown in FIGS. 13 and 14 to anchor the fixation plate 12 and fixation screws 22 in place adjacent the bone cortex bc. Of course, the procedure may include predrilling before insertion of the fixation screws 22 if necessary.

Figure 15:
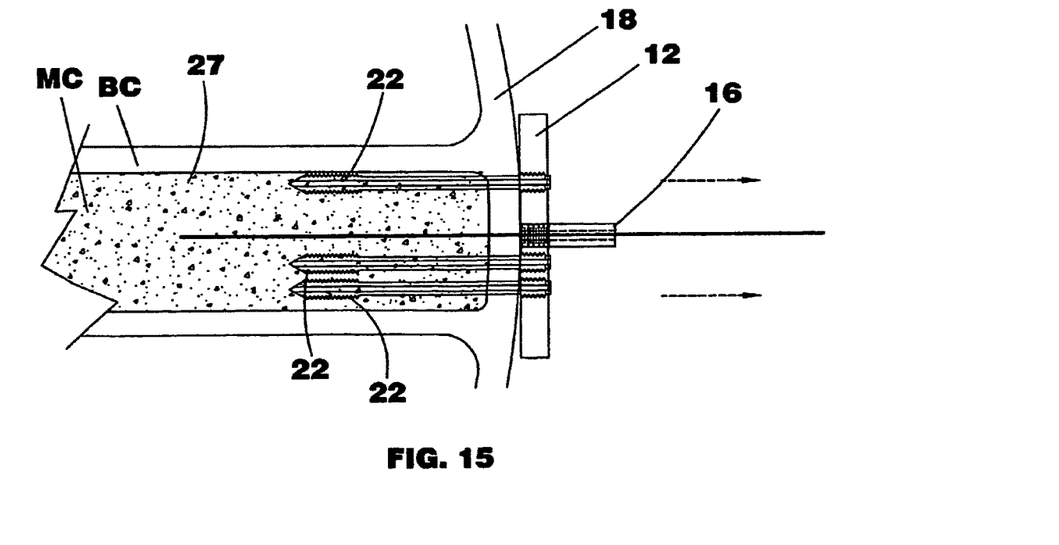
FIG. 15 is a partial cross-sectional side elevation view of the bone end (epiphysis) fracture fixation device of this invention with the alignment guide pin operatively mounted to the fixation plate and the alignment guide pin operatively inserted into the marrow channel mc with the fixation screws anchored into the marrow channel mc with the fixation screw guide wires withdrawn from the marrow channel mc.

As shown in FIGS. 15 and 16, after inserting and anchoring the fixation screws 22 in the marrow channel mc with the distal threads and attaching the fixation screws 22 to the fixation plate 12 with the proximal threads 30 employing a hex head 32 or the like (FIG. 18), the alignment guide pin 16 and the alignment guide wire 24 are removed by the surgeon to complete the procedure as shown in FIG. 17.

Figure 19:
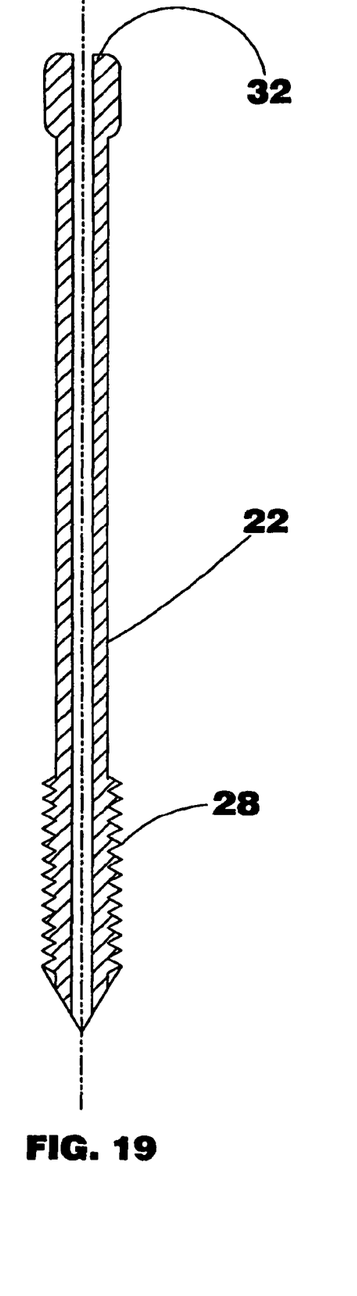
FIG. 19 is a cross-sectional side view of an alternate embodiment of the fixation screw of this invention.

FIG. 19 shows an alternate embodiment of a fixation screw 22 including an enlarged head or tip 32.

Figure 20:
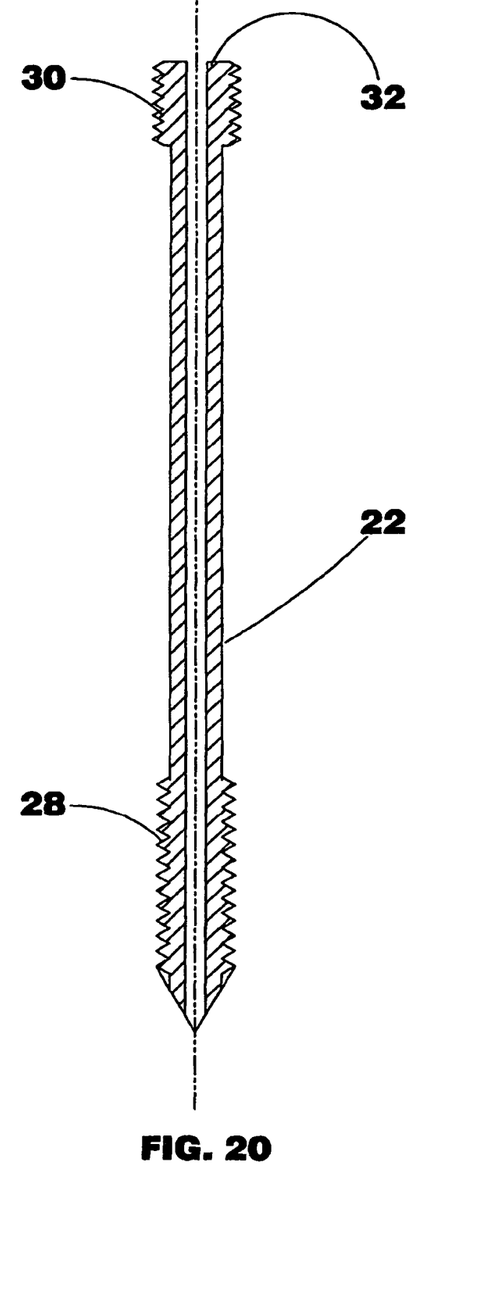
FIG. 20 is a cross-sectional side view of another alternate embodiment of the fixation screw of this invention.

FIG. 20 shows another alternate embodiment of a fixation screw 22 with proximal threads 30 and an enlarged head or tip 32.

The method or procedure of using the bone end (epiphysis) fracture fixation device of this invention comprises the following steps:
  placing the fixation plate 12 on the fractured femur 18,
  centering the alignment guide pin aperture 14 of the fixation plate 12 on the fractured femur 18 relative to the marrow channel mc,
  mounting the alignment guide pin 16 on the fixation plate 12 in coaxially alignment relative to the alignment guide pin aperture 14,
  inserting the alignment guide wire 24 through the alignment guide pin 16 and into the center of the marrow channel mc,
  rotating the fixation plate 12 about the alignment guide wire 24 to align at least two fixation screw apertures 20 relative to the bone cortex be or cordial bone,
  mounting a fixation screw guide pin 25 on the fixation plate 12 in concentric alignment or registry with each of the selected fixation apertures 20 disposed substantially perpendicular to the fixation plate 12 and substantially parallel to the alignment guide pin 16,
  inserting a fixation screw guide wire 27 through each fixation screw guide pin 25 into the marrow channel mc disposed in substantially parallel relationship to each other and the alignment guide wire 16,
  removing each fixation screw guide pins 25 from the fixation plate 12,
  placing a cannulated fixation screw over each fixation screw guide wire 27,
  inserting each cannulated fixation screw into the marrow channel mc such that the peripheral of each cannulated fixation screw 25 is disposed (immediately) adjacent the bone cortex be or cordial bone to anchor the fixation plate 12,
  removing each fixation screw guide wire 27 and,
  removing the alignment guide pin 16 and the alignment guide wire 24 from the fixation plate 12.

While the above detailed description has been made with regard to the use of preferred embodiments for fixing a femoral neck fracture, it is to be remembered that the scope of the present invention is not limited to fractures of the femoral neck. The fracture fixation device of this invention is suitable for use in a variety of conditions wherein a bone end (epiphysis) fracture is involved such as, for example only, a fracture involving the proximal humerus or a fracture of the distal femur.

It will thus be seen that the objects set forth above, among those made apparent from the preceding description, are efficiently attained and, since certain changes may be made in the constructions set forth and in carrying out the above method without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A method of affixing a bone end (epiphysis) fracture fixation device to the neck of a fractured femur bone including a fixation plate and a plurality of fixation screws comprising the steps of:
  placing the fixation plate including a centering alignment guide pin aperture on the fractured femur disposed substantially perpendicular to a central axis of the neck of the femur bone;
  aligning the centering alignment guide pin aperture of the fixation plate with a center of the marrow channel of the neck of the fractured femur bone;
  mounting an alignment guide pin on the centering alignment guide pin aperture of the fixation plate;
  inserting an alignment guide wire through the alignment guide pin and into the center of the marrow channel of the neck of the fractured femur bone;
  rotating the fixation plate about the alignment guide wire to align at least two fixation screw apertures relative to the bone cortex;
  mounting fixation screw guide pins on the fixation plate in concentric alignment or registry with corresponding fixation apertures formed through the fixation plate and disposed substantially perpendicular to the fixation plate and substantially parallel to the alignment guide pin;
  inserting a fixation screw guide wire through each fixation screw guide pin into the marrow channel disposed in substantially parallel relationship to each other and the alignment guide wire;
  removing each fixation screw guide pin from the fixation plate;
  placing a cannulated fixation screw over each fixation screw guide wire;
  inserting each cannulated fixation screw into the marrow channel such that a periphery of each cannulated fixation screw is disposed adjacent the bone cortex to anchor the fixation plate;
  removing each fixation screw guide wire; and
  removing the alignment guide pin and the alignment guide wire from the fixation plate.

* * * * *